US00PP35609P2

(12) United States Plant Patent
Farrow

(10) Patent No.: US PP35,609 P2
(45) Date of Patent: Jan. 30, 2024

(54) ***CAMELLIA* PLANT NAMED 'FARROWCJFRF'**

(50) Latin Name: ***oleifera* x *sasanqua***
Varietal Denomination: FARROWCJFRF

(71) Applicant: Spring Meadow Nursery Inc., Grand Haven, MI (US)

(72) Inventor: Michael W. Farrow, Warwick, MD (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 0 days.

(21) Appl. No.: 18/109,625

(22) Filed: Feb. 14, 2023

(51) Int. Cl.
*A01H 5/02* (2018.01)
*A01H 6/00* (2018.01)

(52) U.S. Cl.
USPC ..... Plt./244

(58) Field of Classification Search
USPC ..... Plt./244
CPC ..... A01H 5/02; A01H 5/00; A01H 6/00
See application file for complete search history.

(56) References Cited

PUBLICATIONS

Teashon, *Camellia sasanqua*—Royalty in the Winter Garden, West Sound magazine, retrieved on Jun. 5, 2023 at https://wsmag.net/the-garden/2018-12-27/camellia-sasanqua-royalty-in-the-winter-garden/#, 2018, 3 pp. (Year: 2018).*

Wilson Bros Gardens, Winter's Fancy *Camellia*, retrieved on Jun. 5, 2023 at https://www.wilsonbrosgardens.com/winters-fancy-camellia-3-gallon.html, 3 pp. (Year: 2023).*

* cited by examiner

*Primary Examiner* — June Hwu
(74) *Attorney, Agent, or Firm* — Cassandra Bright

(57) ABSTRACT

A new and distinct cultivar of *Camellia* plant named 'FARROWCJFRF' is disclosed, characterized by light pink single to semi-double flowers, and dark reddish-purple foliage color on the new flush of growth. Mature foliage is dark green with a glossy cuticle. The new cultivar is a *Camellia*, suitable for ornamental garden purposes.

3 Drawing Sheets

Latin name of the genus and species: *oleifera* x *sasanqua*. Variety denomination: 'FARROWCJFRF'.

BACKGROUND OF THE INVENTION

The new cultivar is a product of a planned breeding program by the inventor. The open-pollination resulting in the new variety was made during 2010, at a nursery in Warwick, Maryland. The seed parent is the unpatented variety *Camellia* 'Winter's Joy'. The pollen parent is unidentified. The inventor discovered this new variety at the same nursery in 2012.

After identifying the new variety as a potentially interesting selection, the inventor first propagated plants of 'FARROWCJFRF' by semi-hardwood vegetative cuttings during 2012 at the same nursery in Warwick, Maryland. Multiple generations have been reproduced and have shown that the unique features of this cultivar are stable and reproduced true to type.

Date of first sale was Jun. 21, 2022, occurring in Grand Haven, Michigan. This sale was made directly by the inventor or one who obtained the claimed invention directly or indirectly from the inventor. This sale and all public disclosures made between Jun. 21, 2022 and the filing of this application fall within the exception allowed under 102(b)(1).

SUMMARY OF THE INVENTION

The cultivar 'FARROWCJFRF' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'FARROWCJFRF' These characteristics in combination distinguish 'FARROWCJFRF' as a new and distinct *Camellia* cultivar:

1. Dark reddish-purple foliage color occurring on new flush.
2. Mature foliage is dark green with a glossy cuticle.
3. Light pink, single to semi-double flowers.
4. Self-cleaning flowers.

COMPARISON TO PARENT VARIETY

'FARROWCJFRF' is similar in most horticultural characteristics to the seed parent variety *Camellia* 'Winter's Joy'. Plants of the new cultivar 'FARROWCJFRF' however, differ in the following:

1. Flowers of the new variety are lighter pink than flowers of the seed parent.
2. Flowers of the new variety are single to semi-double, while flowers of the seed parent are fully double.
3. Foliage of the new variety has a vibrant, dark purple new flush, while foliage of the seed parent has a less distinctive new flush color.

COMMERCIAL COMPARISON

'FARROWCJFRF' can be compared to the commercial variety *Camellia* 'Winter's Fancy', unpatented. Plants of the new cultivar 'FARROWCJFRF' are similar to plants of 'Winter's Fancy' in most horticultural characteristics, however, plants of the new cultivar 'FARROWCJFRF' differ in the following:

1. Foliage of the new variety has a vibrant, dark purple new flush, while foliage of this comparator does not have a vibrant flush color.

BRIEF DESCRIPTION OF THE PHOTOGRAPHS

The accompanying photograph in FIG. 1 illustrates in full color a plant of 'FARROWCJFRF' grown outdoors in Grand Haven, Michigan, having the distinctive dark purple flush.

Figure 1:
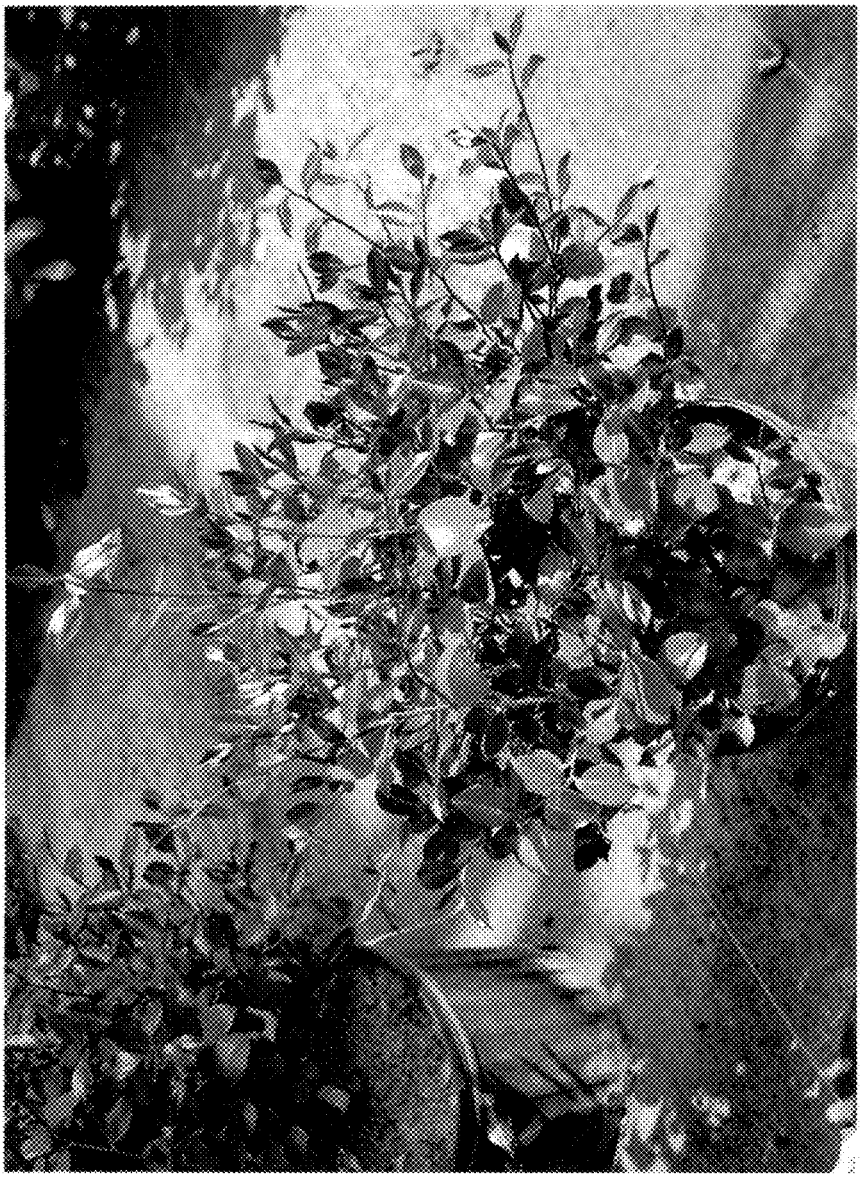
Figure 2:
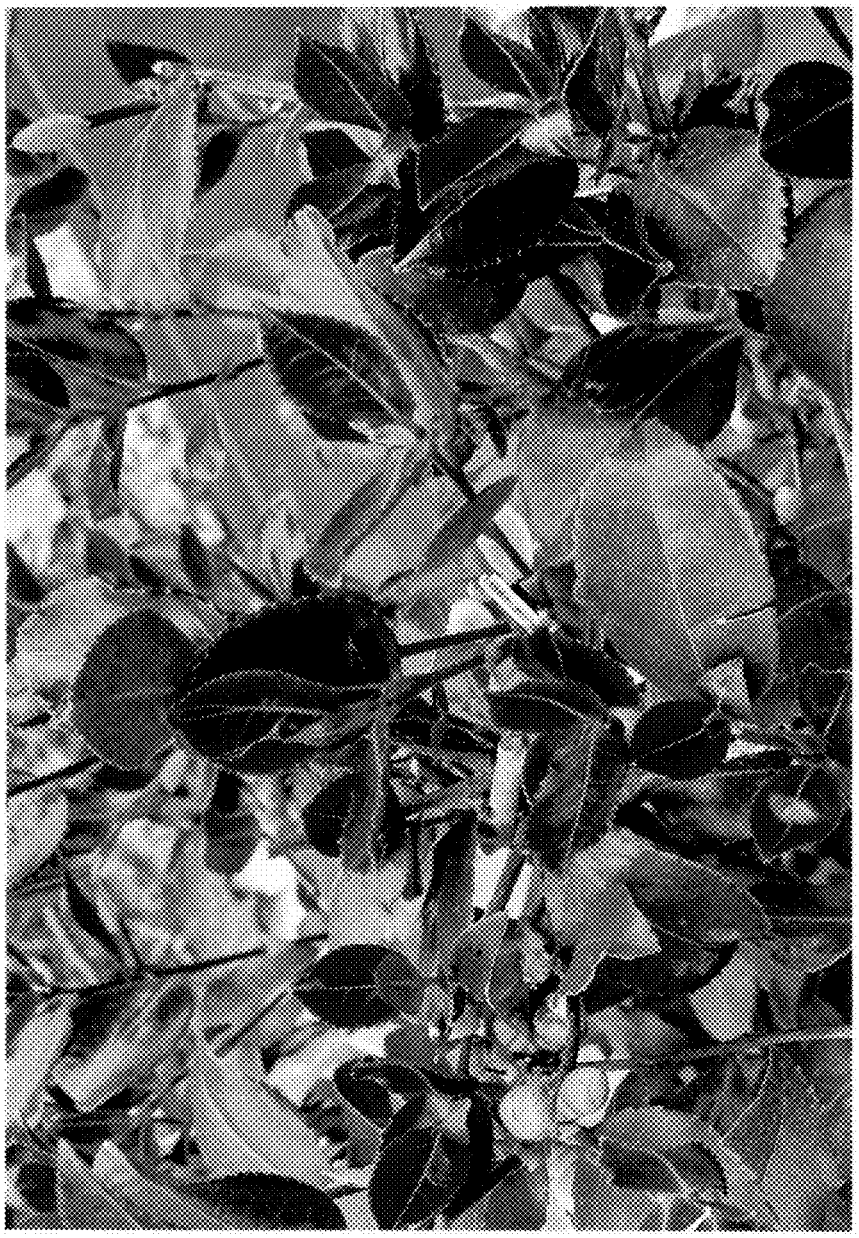
FIG. 2 shows a closer view of the new flush coloration on plants of the new variety.
Figure 3:
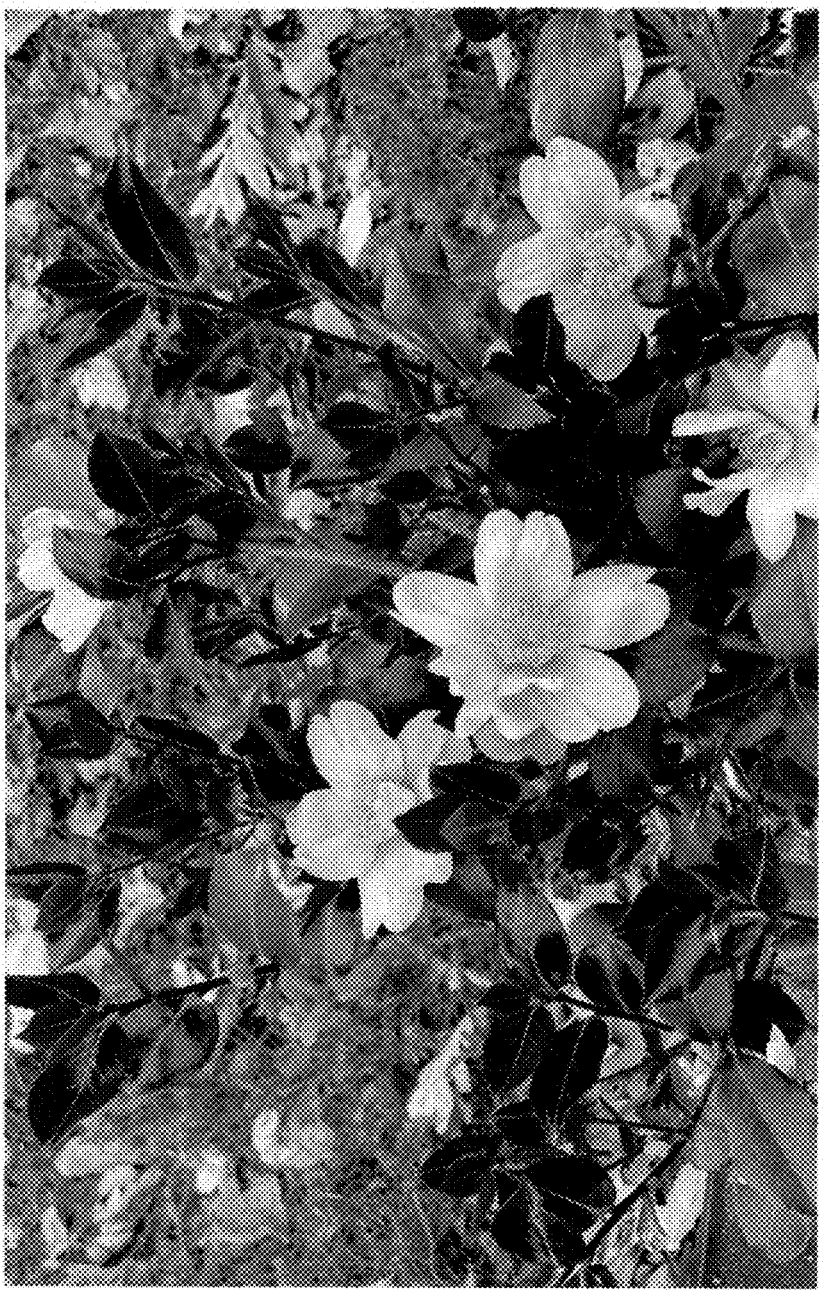
FIG. 3 illustrates a typical flowering plant of the new variety. Plants photographed are approximately 18 months old.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'FARROWCJFRF' plants grown in a poly-greenhouse in Grand Haven, Michigan in the fall of 2021. Plants are approximately 2 to 3 years old, in 3-gallon containers. The average day time temperature is 18-27° C., average night temperature is 5-10° C. Measurements and numerical values represent averages of typical plant types.

Botanical classification: *Camellia oleifera* x *sasanqua* 'FARROWCJFRF'.

PROPAGATION

Method: Hardwood cuttings.
Time to rooting: 4 weeks at 18-27° C.
Root description: Moderately dense, freely branching, thin, and fibrous. Light brown to tannish-white in color, not accurately measured by the color chart.

PLANT

Plant type: Evergreen flowering shrub.
Plant shape: Upright, somewhat mounded.
Growth habit: Upwards and outwards.
Height: 60 cm.
Plant spread: 55 cm.
Growth rate: Moderate.
Plant vigor: Good.
Branching characteristics:
- *Lateral branches*.—Branching Habit: Basal. Quantity: 25 to 30. Length: 35 cm. Diameter. 3 mm.
- *Stem*.—Shape: Rounded. Aspect. 70° to 90°. Strength: Strong, quite rigid. Pubescence: Some, on new growth only. Color: New Growth: RHS Greyed-Orange 176A. Old Growth: RHS Grey-Brown 199A-B.
- *Internode*.—3 cm.

FOLIAGE

Leaf:
- *Type*.—Single.
- *Arrangement*.—Alternate.
- *Length*.—6 cm.
- *Width*.—3.5 cm.
- *Shape*.—Elliptic.
- *Apex*.—Acute.
- *Base*.—Obtuse.
- *Margin*.—Serrulate.
- *Texture of top surface*.—Smooth, very glossy.
- *Texture of bottom surface*.—Smooth, glossy.
- *Density*.—Moderate to dense.
- *Color*.—Young foliage upper side: Near RHS Purple N77A. Young foliage under side: Near RHS Brown 200B. Mature foliage upper side: RHS Green NN137A. Mature foliage under side: RHS Yellow-Green 147B.
- *Venation*.—Type: Pinnate. Venation color upper side: RHS Yellow-Green 147B. Venation color under side: RHS Yellow-Green 147B.

Petiole:
- *Length*.—5 mm.
- *Diameter*.—2 mm.
- *Texture*.—Somewhat pubescent, soft.
- *Color*.—RHS Yellow-Green 147B.

FLOWER

Bloom period: Fall.
Flowers:
- *Arrangement*.—Single or paired flowers at leaf nodes along length of lateral branches.
- *Shape*.—Single whorl.
- *Aspect*.—Outwards from lateral stem.
- *Quantity of flowers per lateral stem*.—3 to 5.
- *Quantity of buds per lateral stem*.—3 to 5.
- *Length*.—6 cm.
- *Diameter*.—6 cm.
- *Depth*.—2 cm.
- *Persistent or self-cleaning*.—Self-cleaning.
- *Fragrance*.—Mildly sweet, spice-like.

Petals:
- *Length*.—3 cm.
- *Width*.—2.5 cm.
- *Apex*.—Retuse.
- *Shape*.—Elliptic to obovate.
- *Margin*.—Entire.
- *Margin undulation*.—Weak.
- *Arrangement*.—Single whorl.
- *Number*.—6 to 8.
- *Fused*.—No.
- *Appearance*.—Smooth.
- *Texture*.—Smooth, soft.
- *Color*.—Upper surface at first opening: RHS Red-Purple 69A, fading to 73C at very base. Under surface at first opening: RHS Red-Purple 69A, fading to 73C at very base. Upper surface at maturity: RHS Red-Purple 69A, fading to 73C at very base. Under surface at maturity: RHS Red-Purple 69A, fading to 73C at very base.

Petaloids: Absent.
Bud:
- *Shape*.—Ovoid.
- *Length*.—1 cm.
- *Diameter*.—0.75 cm.
- *Color*.—RHS Yellow-Green 146C.

Sepals:

*Length*.—1.8 cm.

*Width*.—1.3 cm.

*Shape*.—Obovate.

*Number*.—5 to 7.

*Color*.—Outer surface: RHS Yellow-Green N144B. Inner surface: RHS Yellow-Green 146D.

Peduncle:

*Length*.—5 mm.

*Diameter*.—3 mm.

*Color*.—RHS Yellow-Green 146C.

*Texture*.—Glabrous.

*Aspect*.—45°.

*Strength*.—Good.

REPRODUCTIVE ORGANS

Stamens:

*Number*.—Average 100.

*Arrangement*.—Apricot.

*Filament length*.—1 cm.

*Filament color*.—RHS Yellow 8C.

*Anthers*.—Length: 2 mm. Color: RHS Yellow 8C. Pollen: Quantity: Sparse to none. Color: RHS Yellow 8C. Shape: Club-like.

Pistil:

*Number*.—1.

*Length*.—1 cm.

*Style*.—Length: 0.75 cm. Color: RHS Yellow-Green 145D.

*Stigma*.—Shape: Forked. Color: RHS Yellow-Green 145D.

OTHER CHARACTERISTICS

Disease and pest resistance: Observed resistance to *Camellia* related leaf diseases powdery mildew and black spot. The exact pathogens are unknown. Neither resistance nor susceptibility to normal pests of *Camellia* observed.

Temperature tolerance: Typical, USDA zones 7-9.

Fruit/seed: Not observed.

What is claimed is:

1. A new and distinct cultivar of *Camellia* plant named 'FARROWCJFRF' as herein illustrated and described.

* * * * *